United States Patent [19]

Schick

[11] 4,352,780
[45] Oct. 5, 1982

[54] DEVICE FOR CONTROLLED INJECTION OF FLUIDS

[75] Inventor: Karl G. Schick, Whitefish Bay, Wis.

[73] Assignee: Fiatron Systems, Inc., Oak Creek, Wis.

[21] Appl. No.: 157,653

[22] Filed: Jun. 9, 1980

Related U.S. Application Data

[63] Continuation-in-part of Ser. No. 57,369, Jul. 13, 1979, Pat. No. 4,272,483.

[51] Int. Cl.³ .................... G01N 21/00; G01N 35/00; G01N 35/08
[52] U.S. Cl. ........................ 422/67; 422/63; 422/68; 422/81; 73/863.71; 73/61.1 R
[58] Field of Search .......... 73/61.1 R, 863.71, 863.72, 73/23.1; 222/395; 141/130; 422/67, 64, 82, 81, 63, 70, 89, 68, 76, 116; 23/230 R, 230 A, 232 C

[56] References Cited

U.S. PATENT DOCUMENTS

| | | | |
|---|---|---|---|
| 2,833,151 | 5/1958 | Harvey | 73/863.72 |
| 3,057,594 | 10/1962 | Allen | 73/863.71 |
| 3,065,060 | 11/1962 | Roehrig et al. | 422/89 |
| 3,285,701 | 11/1966 | Robertson | 422/89 |
| 3,479,880 | 11/1969 | Mutter et al. | 73/422 |
| 3,501,961 | 3/1970 | Hable et al. | 73/863.72 |
| 3,649,203 | 3/1972 | Schneider | 422/81 |
| 3,653,840 | 4/1972 | Silas | 73/23.1 |
| 3,690,833 | 9/1972 | Ferrari | 23/230 R |
| 3,858,450 | 1/1975 | Jones | 73/863.72 |
| 3,881,872 | 5/1975 | Naono | 23/230 R |
| 4,013,413 | 3/1977 | Stewart et al. | 23/230 R |
| 4,022,575 | 5/1977 | Hanson et al. | 23/230 R |
| 4,102,648 | 7/1978 | Hartmann et al. | 422/54 |
| 4,108,602 | 8/1978 | Hanson et al. | 422/81 |
| 4,148,610 | 4/1979 | Miller et al. | 422/81 |
| 4,272,483 | 6/1981 | Schick | 73/863.71 |

FOREIGN PATENT DOCUMENTS

2806157 10/1978 Fed. Rep. of Germany ........ 422/81

*Primary Examiner*—Kenneth M. Schor
*Attorney, Agent, or Firm*—McDougall, Hersh & Scott

[57] ABSTRACT

A device for flow injection analysis wherein use is made of a double loop connected at opposite ends with flow control valves for alternate simultaneous injection of sample fluid in one loop while electrolyte fluid is injected in the other and for simultaneous alternate flow from one loop to an analysis station and from the other loop to a collector, and means for controlling the valves and pumps associated with the first valve for regulating the amount of sample fluid and electrolyte displaced through said valves.

11 Claims, 17 Drawing Figures

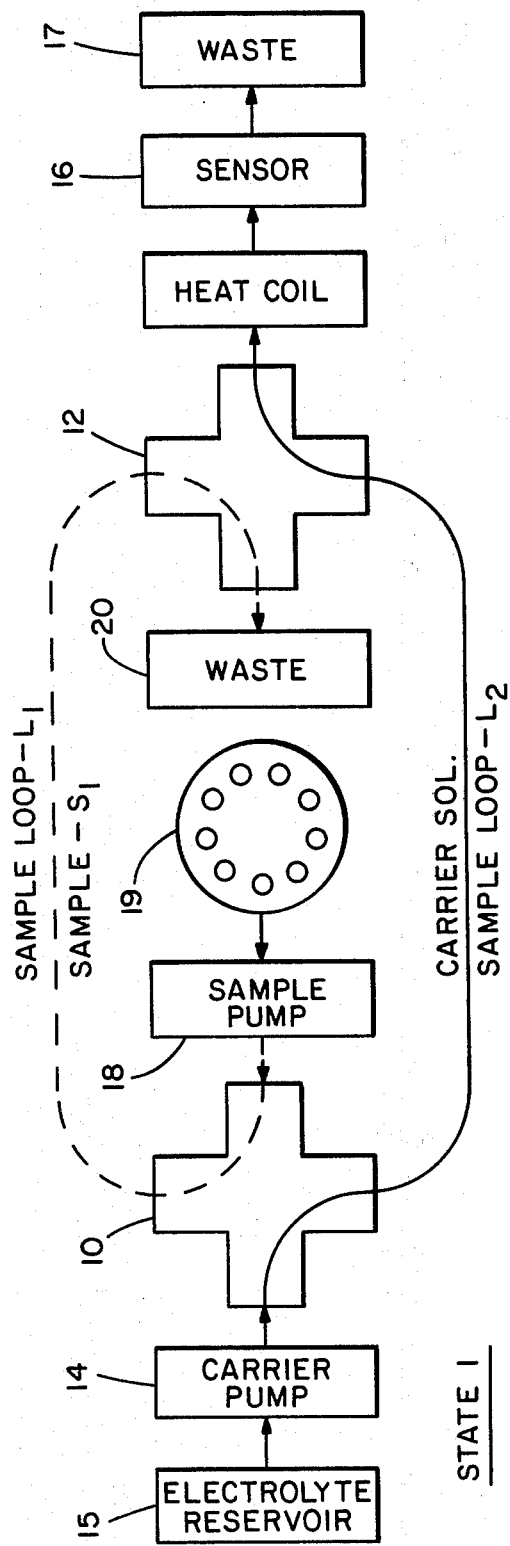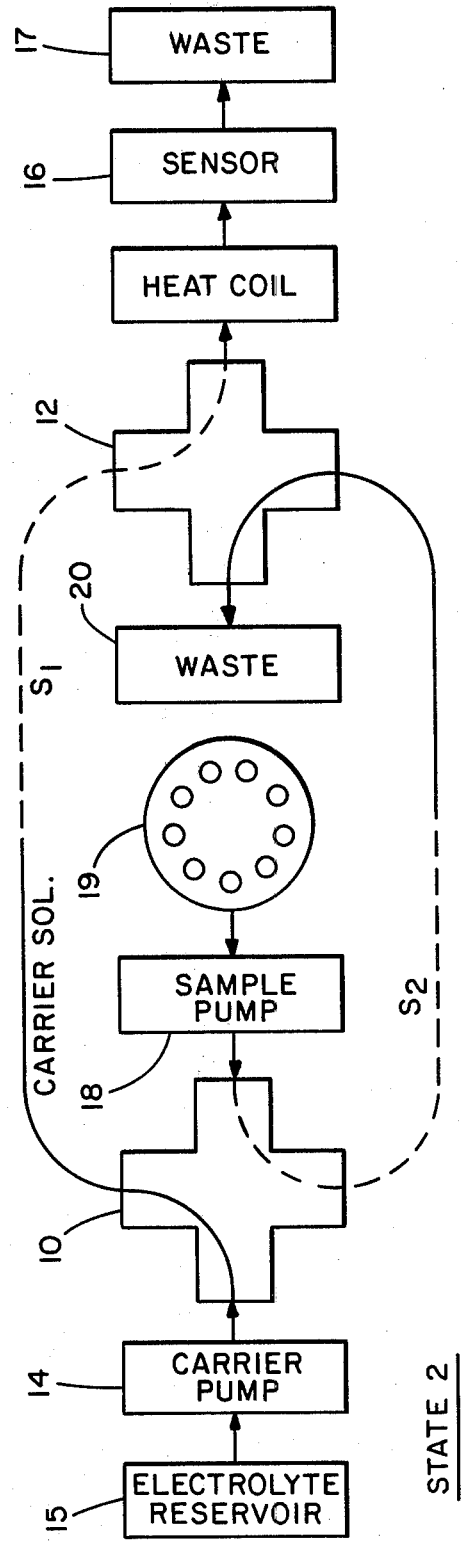

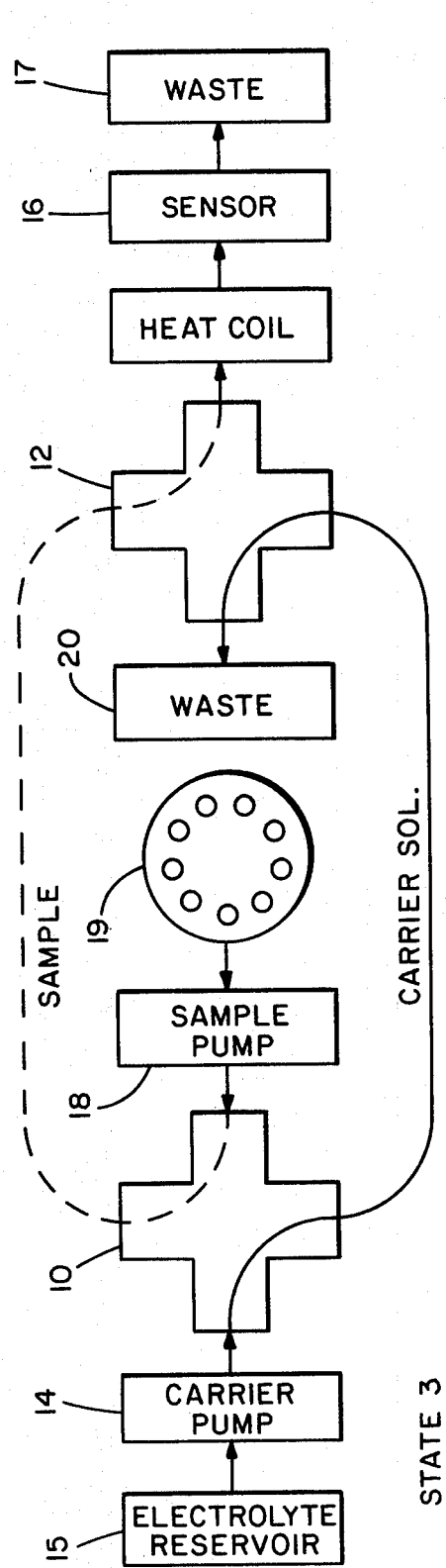
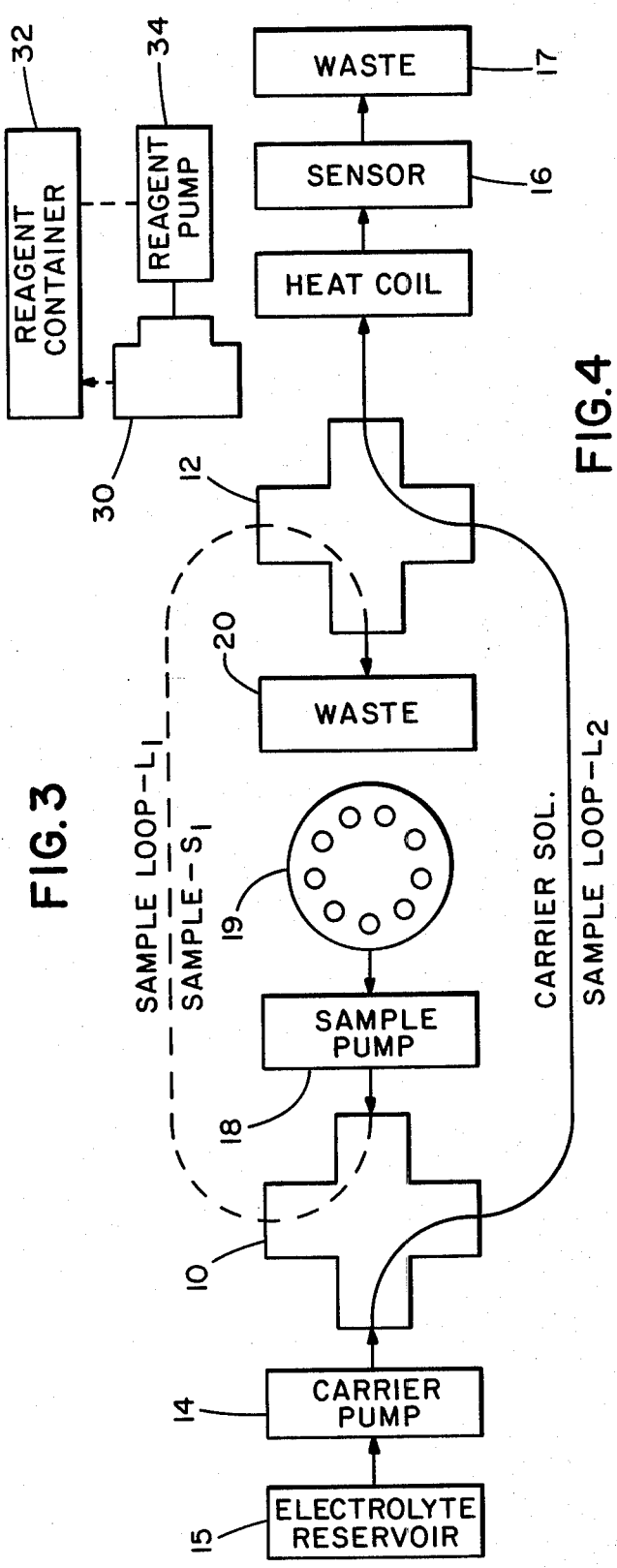

STATE 4

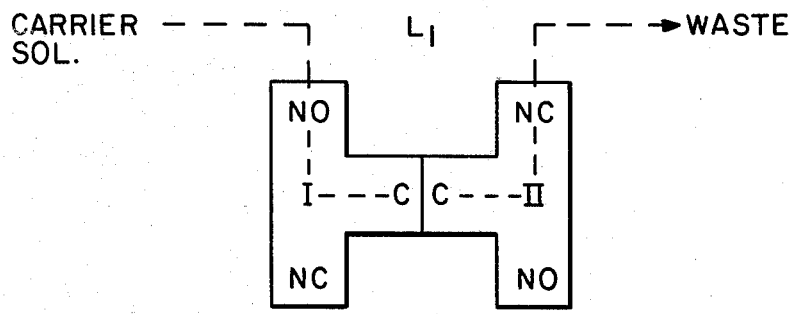
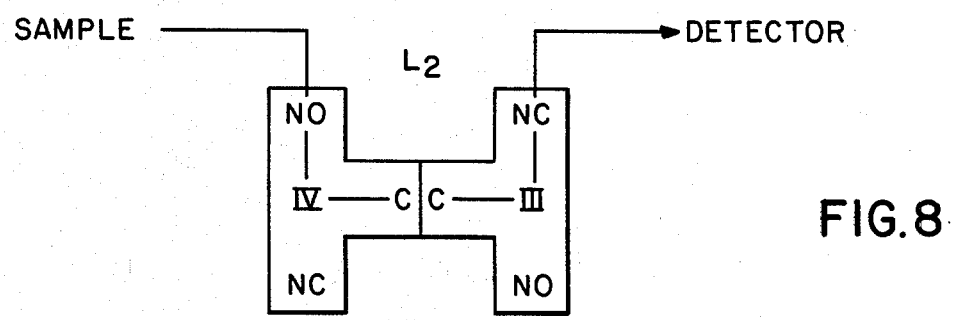
$V_I$ = OFF   $V_{II}$ = ON
$V_{IV}$ = OFF   $V_{III}$ = ON
FIG. 8
STATE 3
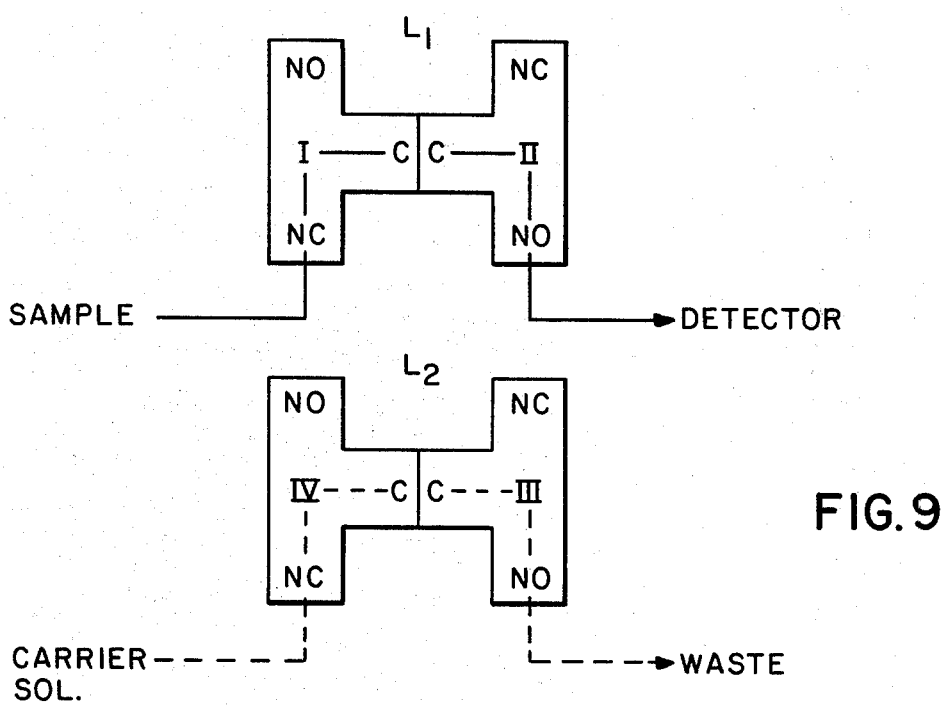
$V_I$ = ON   $V_{II}$ = OFF
$V_{IV}$ = ON   $V_{III}$ = OFF
FIG. 9
STATE 4

MODE 1: FIXED SAMPLE VOLUME

MODE 2: VARIABLE SAMPLE VOLUME

MODE 3: POINT SOURCE SAMPLING

MODE 4: STOP-FLOW

NOTE: $T_3$ = PULSE WIDTH FOR SAMPLE SOLUTION
$T_4$ = PULSE WIDTH FOR CARRIER SOLUTION

DEVICE FOR CONTROLLED INJECTION OF FLUIDS

This is a continuation-in-part of my copending application Ser. No. 57,369, filed July 13, 1979 (now U.S. Pat. No. 4,272,483) entitled "Solution Handling Apparatus and Method."

This invention relates to solution handling systems adapted for continuous flow of controlled amounts of liquid medium to be analyzed, as in continuous flow analysis.

In my aforementioned copending application, description is made of an apparatus which makes use of a carrier pump and a sample pump, with the carrier pump connected to a source of carrier fluid and with the sample pump connected to the sample source, with the pumps connected by a pair of separated multiple valve means to form a pair of loops of predetermined volume whereby in one state, $sample_1$ is circulated between the valves for filling the loop with $sample_1$ while carrier or electrolyte liquid is circulated through the other loop to displace the volume of $sample_2$ from the loop to a detector device and, in a second state, $sample_3$ is circulated through the other loop while carrier liquid is circulated through the first loop to displace the volume of $sample_1$ to the detector device. Thus volumetrically measured amounts of samples are displaced in sequence, in continuous flow from sample sources to a detector for analysis.

The operation capable of being carried out by the flow injection apparatus of the described copending application are depicted in FIGS. 1 and 2, hereinafter referred to as states 1 and 2 respectively. When the valves 10 and 12 are in the positions of adjustment shown in state 1, the carrier electrolyte or liquid is displaced by carrier pump 14 from a source 15 of carrier liquid through loop $L_2$ to a detector 16 where the volume of sample swept from loop $L_2$ is analyzed during flow therethrough to waste 17. Concurrently, sample liquid is directed by the valve 10 for circulation by the sample pump 18 from a sample source 19 for circulation through loop $L_1$ to the valve 12 which directs sample liquid flowing therethrough to waste 20. Thus, while sample loop $L_2$ is delivering sample $S_1$ to the detector, sample loop $L_1$ is being filled with the next liquid sample.

When the valves 10 and 12 are displaced to the position shown in state 2 of FIG. 2, the carrier electrolyte stream is directed by the valve 10 from the carrier pump 14 into loop $L_1$ for transport of sample $S_2$ in the loop to the detector. Simultaneously a new sample $S_3$ is directed by the valve 10 from the sample pump 18 into loop $L_2$ to fill the loop with sample, with excess going to waste. Thus the switching action from state 1 to state 2 results in the introduction of fixed volumes of sample into the carrier electrolyte stream.

Analysis of liquid samples provided by the described apparatus operating between states 1 and 2 is based entirely on a volumetric concept which allows for the transmission of signals rising to sharp peaks as read by the detector from the sample stream as diluted by the electrolyte.

It is an object of this invention to produce an apparatus of the type described wherein the types of detectors and analyzers with which the apparatus may be used is greatly expanded to include testing procedures incapable of being carried out by the fluid handling device previously described; which operates on a time relationship whereby the size of the sample can be varied to accommodate analyses for steady state signals; wherein pressure drop across the valves is minimized or made substantially constant; in which the flow of sample can be stopped for sample analysis whereby programmable volumes of liquid, sampling rate and number of repetitive samples can be programmed by associated software; which embodies digitally controlled sample injection; and which is self cleaning thereby to eliminate the need for a wash cycle; and in which reagents can be incorporated into the sample for flow through the sample loop or otherwise introduced for admixture before the sample reaches the detector.

These and other objects and advantages of this invention will hereinafter appear and for purposes of illustration, but not of limitation, an embodiment of the invention is shown in the accompanying drawings in which:

FIGS. 1–5 illustrate the various states in which the apparatus of the invention can operate;

FIGS. 6–9 illustrate the four way valve connection in the various states illustrated in FIGS. 1–5;

Figure 5:
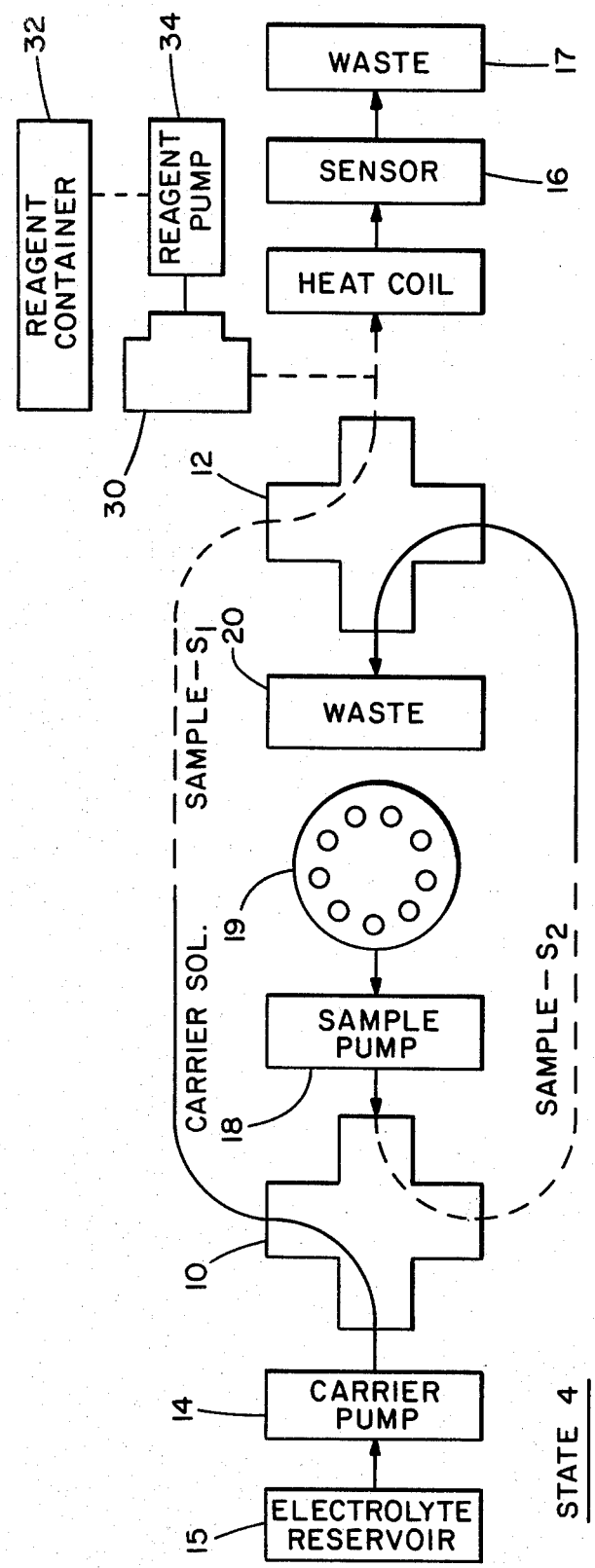

When the valves are in state 1, the carrier liquid is pumped through loop $L_2$ to the detector 16 while the sample is pumped through loop $L_1$ to waste. Thus the sample $S_0$, originally in the loop $L_2$, is displaced by the carrier liquid to the detector while the loop $L_1$ is being filled with sample $S_1$.

When the valves are in state 2, the carrier liquid is pumped through the loop $L_1$ to displace sample $S_1$ to the detector while new sample $S_2$ is pumped through loop $L_2$ to waste. Thus the sample $S_1$ is displaced from loop $L_1$ by the carrier liquid to the detector while the loop $L_2$ is being filled with the sample $S_2$.

When as described in the aforementioned copending application, the sample pump is located downstream of the second valve, between the valve and the waste, the apparatus is incapable of operation in any state other than the described states 1 and 2. This limits the apparatus to samples based on the volume of the loops $L_1$ and $L_2$ and thus restricts the utilization that can be made of the apparatus for various test procedures that are not volumetric in nature. It has been found that the number and types of analyses can be greatly expanded for use in tests when the sample pump is located upstream of the valving at the head end of the loops and when use is made of means for controlling valve operations to predetermined time intervals, as by programmable computerized control.

The time intervals, hereinafter referred to as $T_1$, $T_2$, $T_3$, $T_4$, $T_5$ and $T_6$ can be programmed, such as with an RCA Microboard Computer or other timed sequencing means, in terms of their respective volumes $V_1$ through $V_5$ of liquid carrier and fluid sample displaced through the loops to the detector and waste.

$T_1$ relates to the time interval that the sample fluid is pumped from the sample holder 19 into the dual channel sample injector described.

$T_2$ represents the minimum time interval between repetitive samplings.

$T_3$ defines the injection sample size based upon time operation of the sample pump.

$T_4$ is the time interval allowed between injections.

$T_5$ determines the time interval between successive sample injections.

$T_6$ refers to the time interval that the pumps are deenergized after $T_3$ so that the sample remains stationary in the detector for examination and for rate measurements.

$T_8$ is the time interval of diluted sample injection.

$T_9$ is the time length of on-stream gradient.

Figs. 6–9 illustrate in diagrammatic form the four way valves formed of a pair of three way valves having a common interconnection and the normal position of each of the valves as well as their positions during each of the operational states illustrated in FIGS. 1–5.

The dual channel sample injector of this invention is operated by the four independent control elements, illustrated as interconnected 3-way valves, each requiring a separate control line. The connecting cable of the device has five leads, four of which are control lines while the fifth is to ground. Each control line is operated with a 12 VDC, 0.38 Amp signal. Each valve state (VS) is defined by a set of ON/OFF signals, illustrated in the following table, and which can be monitored via a front panel status indicator (not shown)

TABLE

| VALVE STATES | CONTROL LINES | | | |
|---|---|---|---|---|
| | V I | V II | V III | V IV |
| 1 | OFF | OFF | OFF | OFF |
| 2 | ON | ON | ON | ON |
| 3 | OFF | ON | ON | OFF |
| 4 | ON | OFF | ON | OFF |

OFF = control line V I, V II, V III, or V IV is not energized.
ON = control line V I, V II, V III or V IV is energized.

FIGS. 10–13 are charts relating time to sample measurement and four of the modes of operation capable of being carried out with the described apparatus, with attached software for programmable timed sequencing means.

Figure 10:
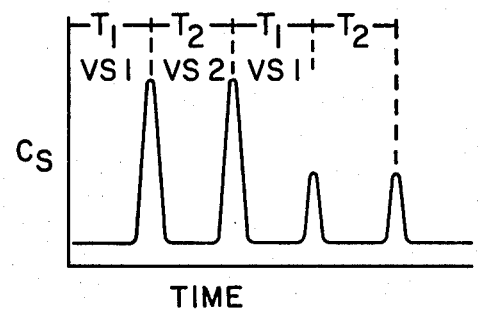
FIGS. 10–13 and 15–17 illustrate the various operational modes of which the apparatus is capable.
Figure 11:
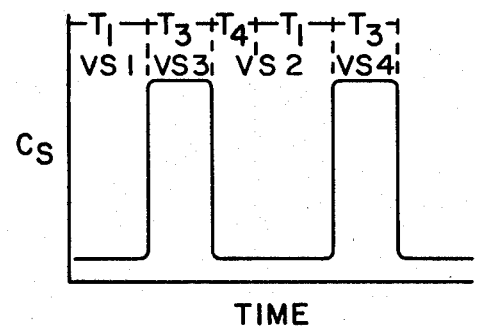
Figure 12:
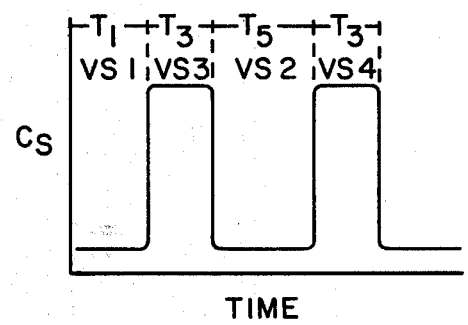
Figure 13:
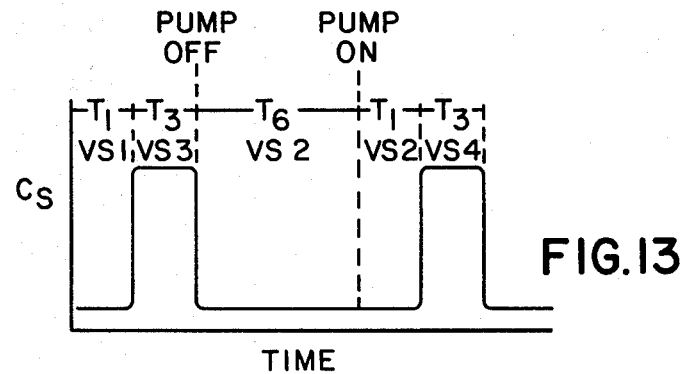
Figure 15:
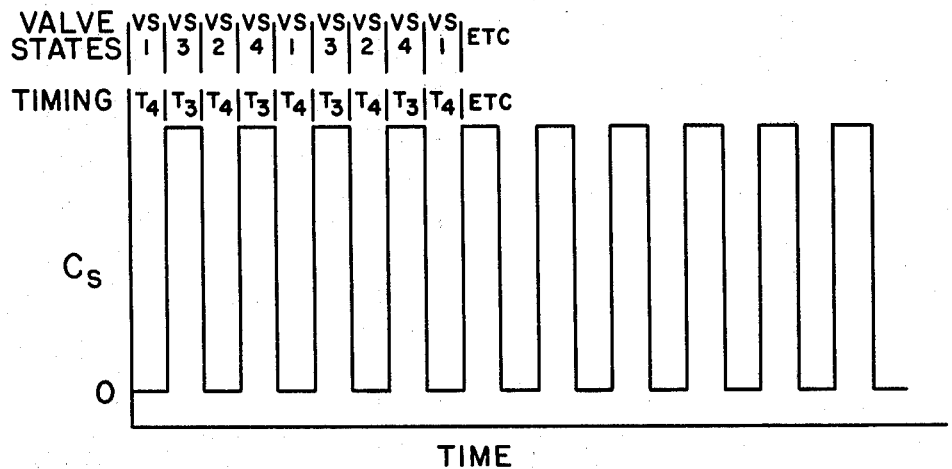
Figure 16:
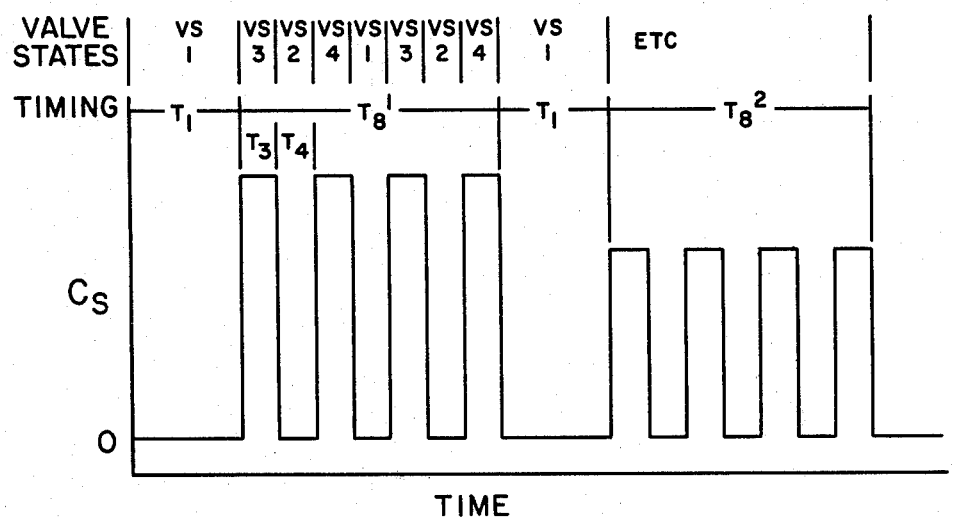
Figure 17:
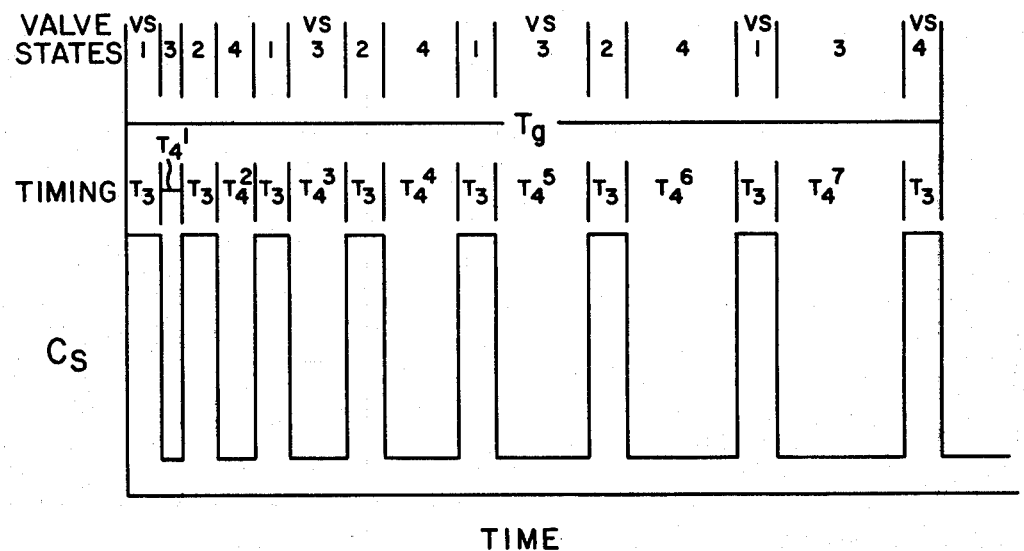

Mode 1, illustrated in FIG. 10, provides for analysis based upon fixed volumes obtained in accordance with states 1 and 2 (FIGS. 1 and 2). During the time interval $T_1$, sample fluid is pumped by the sample pump from the fluid sample holder into the dual channel sample injector and a fixed volume of sample is injected. In the event that repetitive sampling is programmed, the sipper connected to the sample pump is retained in the sample fluid until the predetermined number of samplings has been carried out. The programmable time interval between repetitive samplings is indicated by $T_2$.

In mode 1 wherein a fixed volume of sample fluid is processed through the loop for continuous flow through the detector, measurement provides sharp or peak signals as determined by the detector in examination of the flowing sample volume diluted somewhat by carrier fluid.

Mode 2 (FIG. 11) provides for a variable sample volume to be introduced into the carrier electrolyte stream of the dual channel sample injector by switching from state 1 (FIG. 1) to state 3 (FIG. 3). The exact sample volume introduced will depend on the timing in state 3 and the pumping rate of the sample pump. By switching to state 3, small as well as large sample volumes can be accommodated without change in the sample loops. In mode 2, the sample loops $L_1$ and $L_2$ need not be completely filled, i.e. sample volumes considerably smaller than the sample loop volumes can be injected into the carrier stream with great precision.

During the time interval $T_1$ in mode 2, sample fluid is pumped from the sample source into the dual channel sample injector to fill the loop. During the time interval $T_3$, the sample pump continues to pump sample fluid into the sample injector for a time period that determines the size of the sample caused to flow through to the detector. This determination is made at a steady state to provide readings in the form of a plateau.

State 3 can thus accommodate slow devices or detectors for a steady state signal. In state 3, sample size can be made so large as to enable samples which are not diluted by carriers. This enables expansion of the use of the device to a much wider range of detectors. Mode 2 of state 3 also permits on stream dilution or the addition of reagent for admixture with the sample before determination by the detector, as illustrated in state 4.

In mode 3, for point source sampling, sample fluid is pumped continuously from a point source into the dual channel sample injector. As in the previous diagrams, $T_1$ is the time interval for filling the loop and $T_3$ indicates the time interval for continued injection of sample as in mode 2. $T_5$ is the time interval between successive samplings.

Mode 4 indicates the stop flow operation wherein the pumps are deenergized to cause the sample to remain stationary in the detector for determination. In mode 4, the time intervals $T_1$ and $T_3$ are the same as in mode 2. During the time interval $T_6$, the sample pump is deenergized. The sample remains stationary in the detector for a predetermined (programmable) period of time. During the time interval $T_6$, rate measurements can also be carried out. At the end of the time interval $T_6$, the same pump starts up again, the detector is flushed with carrier solution during time interval $T_1$, and a new sample is introduced into the opposite loop. Mode 4 enables sample flow to be stopped for examination of small samples over an extended period of time.

In state 4, the reagent valve 30 is open to direct the flow of reagent fluid from a container 32, in metered amounts, into the passing sample volume flowing to the detector. Between sample injections in state 4, the reagent solution is recirculated within the reagent cycle by the continuously operating reagent pump 34 thereby to provide for more economical use of costly reagents. The reagent valve can also be programmed for continuous additions of reagent.

In mode 5 on-stream sample or reagent dilution can be attained by alternating between sample or reagent injection ($T_3$) and carrier solution injection ($T_4$). The required valve state (VS) sequence involves VSI→III→II→IV→I→III etc. The dilution ratio is determined by $(T_4+T_3)/T_3$. For optimal results $T_4+T_3 < 1000$ msec. and $T_3 \approx 10$ msec. Short pulses for $T_3$ and $T_4$ are chosen to ensure rapid and complete on-stream mixing of the sample and carrier pulses. For large dilution rations ($T_4 >> T_3$), the "detection" port of the dual channel sample injector is connected to a tangential flow mixing chamber which generates a localized high turbulence flow region thus ensuring a homogeneously diluted sample or reagent stream.

Mode 6 is concerned with programmable sample injection with simultaneous sample dilution. This mode is similar to mode 2. During $T_1$, the sample is pumped from a sample changer or point source into the dual channel sample injector. During $T_8^1$ sample $S_1$ and carrier solution is injected while during $T_8^2$ sample $S_2$ is diluted on-stream. During $T_8$, the alternating sample and carrier injections (see mode 5) allow precise dilution of the sample.

Mode 7 has to do with programmable on-stream gradient formation. During time interval $T_9$ the carrier pulse $T_4$ is linearly decreased while the sample pulse $T_3$ remains constant. Upon mixing of the carrier and sample pulses, a linear sample gradient is formed. The change in $T_4$ is a programmable function of time, $\Delta T_4 = f$ (time). In general, this function can be linear, nonlinear, increasing or decreasing with time. The graph shows the on-stream generation of a binary gradient. However, the formation of a ternary gradient, i.e. a gradient formed from three miscible components can be generated by first forming a binary gradient with the dual channel sample injector of this invention and then superimposing an additional gradient by means of the programmable reagent valve.

The device described is capable of multiple other uses, such as for dispensing predetermined volumes of solution which can be metered into separate containers. It also can be used for calibration of the flow rate of carrier electrolyte and sample fluid as by the determination of the time required to dispense a predetermined volume of liquid as measured in a container of fixed volume.

In practice, the carrier liquid for fluid pumps can be operated continuously except for the period $T_6$. Because of the valve arrangement, surges are completely avoided and pressure drops across the valves remain constant.

The ability to increase or decrease the size of the sample makes it possible to operate the device as a self cleaning device wherein the carrier liquid not only transfers the sample plug but sufficient volume can be injected to clean the loop whereby carryover between samples becomes insignificant.

It will be apparent from the foregoing that many advantages are derived from the solution handling system of this invention. For example, the dual channel sample injector can accommodate small as well as large volumes of sample or reagent without the need to change the sample loops. The device is self cleaning thereby to avoid timely and costly wash or cleaning cycles. The injection of sample into one loop while filling the other loop are carried out simultaneously to provide significant savings in time in the examination of samples. Finally, the use of electrically driven solenoid valves for determining the flow of sample and reagent and the simple on/off logic of sampling arrangement, permits the system to be adapted to digital control.

The device described is capable of numerous additional applications such as in ultraviolet (UV), visible (Vis), infrared (IR) and fluorescence examination of samples; liquid chromatographic and atomic absorption (AA), atomic emission (AE), inductively coupled plasma atomic absorption (ICP) and flame photometry.

IN UV, Vis, IR or fluorescence, reagents necessary for a particular analysis can be present in the carrier liquid. Additional reagents can be added to the streams through operation of the programmable reagent valve.

The device permits synchronized addition of predetermined volumes of sample liquid and reagents so that slow analytical reactions, as in enzyme analysis, can be automated by mode 4.

In use in liquid chromatography, sample introduction and elution can be carried out for low pressure liquid chromatography and very large and very small sample sizes can be readily accommodated.

In AA, AE and ICP and flame photometry, the device provides for sample introduction into flame or plasma at predetermined (programmable rates). Precision can be enhanced by the repetitive sample capability of the device, as in mode 3. The same introduction can be regulated to give either a transient (mode 1) or steady state (mode 2 or 3) signals. In addition, on stream matrix modifications can be provided.

In the AA, AE, ICP and Flame Photometry procedures, it is desirable to reduce the size of the sample without in any way modifying the sample.

Figure 14:
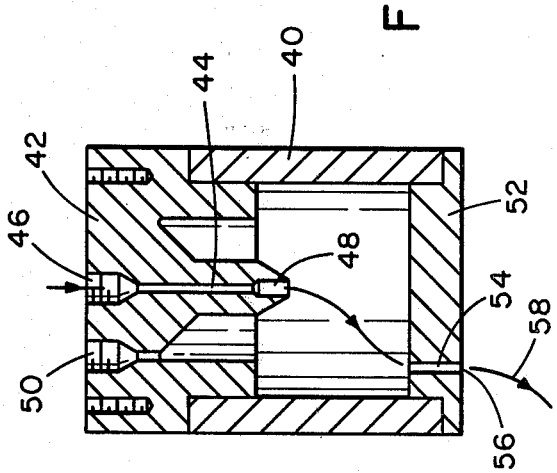
FIG. 14 is a schematic sectional elevational view (upside-down) of a sampler adapted for use in ICP AA and AE analysis in connection with the apparatus of this invention.
Figure 6:
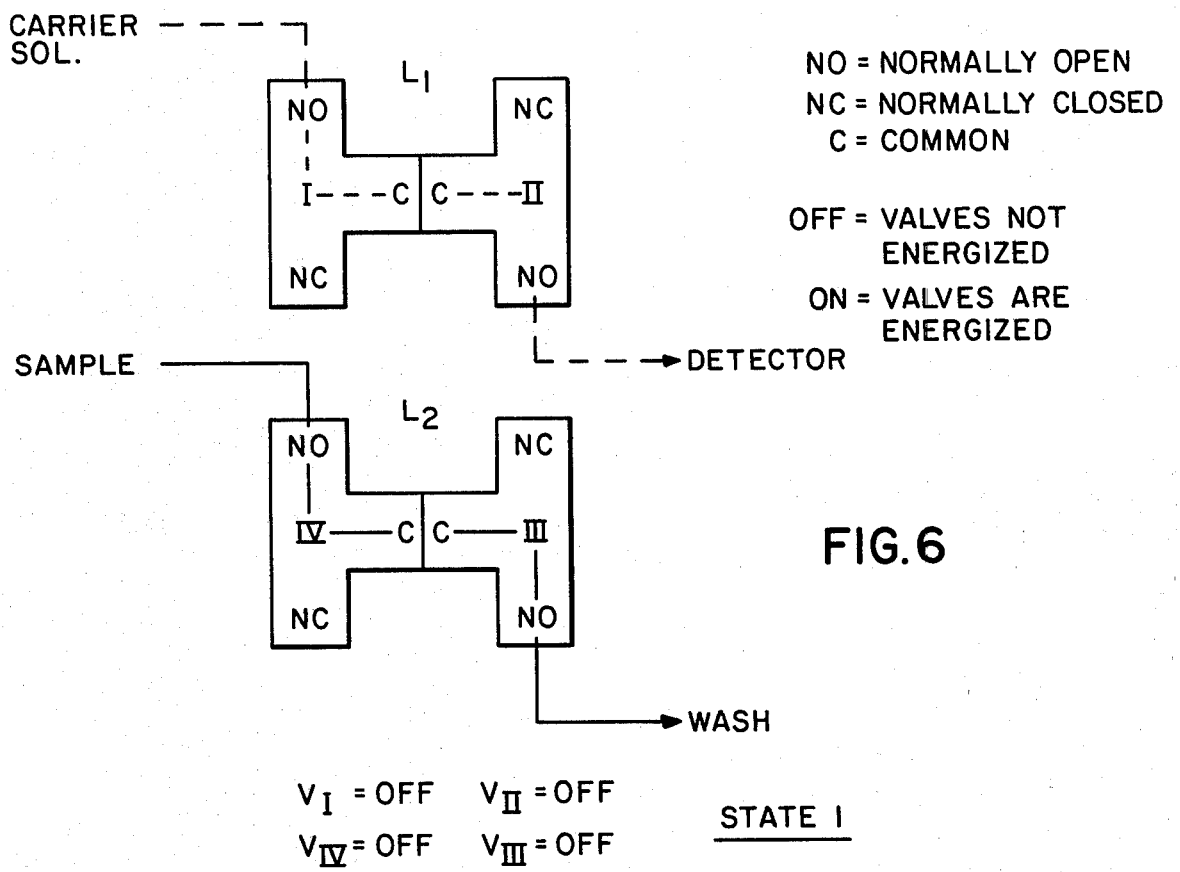
Figure 7:
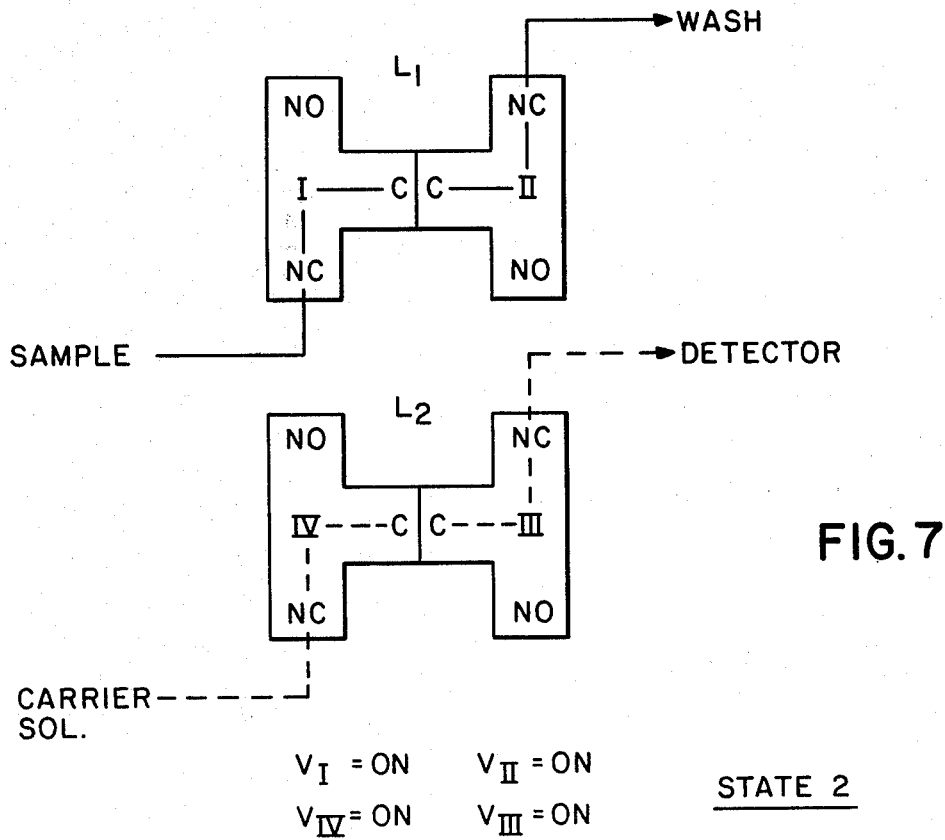

In FIG. 14, there is shown a means for achieving the desired results comprising a cylindrical section 40 of a transparent glass or plastic, such as lucite, in which the cylindrical section is open at both ends. A plug 42, which may be formed of Teflon or other suitable plastic material, is fitted into one open end to form the bottom wall of the tubular housing. The plug is formed with an elongate narrow passage 44 through which the fluid to be tested flows from an inlet 46 into the interior of the housing with the passage 44 emptying into a concentric outlet 48 of larger dimension than the passage. The plug is also formed with an outlet 50 of larger dimension offset laterally from the inlet. The other or top end of the housing is closed by a plug 52 of Teflon or other plastic having a passage 54 of small dimension extending axially therethrough but offset from the passage 44 and spaced a considerable distance therefrom. The outlet 56 from passage 54 is connected to an aspirating tube 58 that leads to the plasma flame. The inlet 46 and outlet 50 in plug 42 are threaded for connection with the sample feed tube and tubing which leads to waste respectively.

In operation, liquid sample is introduced in continuous flow through the inlet 46 for flow through the passage 44 into the interior of the housing. Within the housing, the liquid is under free flow so that air bubbles can escape. By reason of the offset of the outlet passage 54 and because of the free flow of the liquid within the housing to an outlet 50 of larger dimension, only a small fraction of the sample liquid free of dust traverses the space between the end of the passage 44 and the outlet 54 for flow of the fraction to the plasma flame. The rest of the liquid sample flows through the outlet 50 to waste or other collection medium if it is desired to save the sample liquid.

The described device provides for at least a four fold increase in productivity. When used with the solution handling system described, the sample reduction device of FIG. 14 is located immediately in advance of the detector 16 but beyond the valve 12.

I claim:

1. A fluid handling device comprising:
   means for supplying an electrolyte fluid,
   means for supplying a fluid sample for analysis,
   first and second fluid carrying channels,
   first four-way valve means for simultaneously injecting said fluid sample into one of said channels and said electrolyte into the other of said channels,
   a fluid displacement pump communicating the means for supplying the electrolyte fluid with said first valve means for displacement of electrolyte to said first valve means,
   a sample pump communicating the means for supplying the fluid sample with said first valve means for displacement of electrolyte to said first valve means, second four-way valve means for simultaneously receiving electrolyte fluid and fluid sample from said channels, means for controlling the operation of said first and second valve means in response to an electrical impulse to direct the simultaneous flow of fluid sample from said first valve means into one of said channels and electrolyte fluid into the other of said channels and for controlling the second valve means for simultaneous flow of electrolyte fluid and fluid sample from said channels and through said second valve means with either the fluid sample or the electrolyte fluid flowing to means for analyzing the fluid sample and the other flowing to means for collecting the fluid, and means for regulating the operation of said first and second valve means in timed relation to control the volume of fluids displaced by the sample pump and the fluid displacement pump.

2. A device as claimed in claim 1 in which said fluid displacement pump and sample pump operate continuously.

3. A device as claimed in claim 1 which includes means for terminating operation of the sample pump while the fluid sample is directed to said means for analyzing the fluid sample.

4. A device as claimed in claim 1 which includes a computer timed in with the valves for control of operation and timed sequence.

5. A device as claimed in claim 1 in which the timed sequence corresponds to the time for filling the channels to provide constant volumetric analysis of sample fluid.

6. A device as claimed in claim 1 in which the timed sequence exceeds the time for filling the channels to provide for steady state analysis.

7. A device as claimed in claim 1 which includes a reagent, supply source means communicating the reagents supply source with the device for injecting reagent fluid for admixture with fluids prior to the analysis device.

8. A device as claimed in claim 7 which includes means for continuously circulating the reagent for continuous flow and valve means for directing reagent to the analysis system from the continuously recirculating reagent fluid.

9. A device as claimed in claim 1 in which said first and second valve means are four way solenoid-operated valves, said first valve means having two inlets and two outlets with one inlet communicating with the means for supplying the electrolyte fluid and the other inlet communicating with the means for supplying the fluid sample, and with one outlet communicating with one channel and the other outle communicating with the other channel, said second valve means having two inlets and two outlets with one inlet communicating with one channel and the other inlet communicating with the other channel, and with one outlet communicating with said means for analyzing the fluid sample, and the other outlet communicating with a collecting reservoir.

10. A solution handling device as claimed in claim 1 in which a sampling device communicates between the second valve means and the analysis device for drawing a fraction of the sample fluid from the second valve means to the sampling device.

11. A solution handling device as claimed in claim 10 in which the analysis device is one that makes use of a plasma flame.

* * * * *